US008763605B2

(12) United States Patent
Jones et al.

(10) Patent No.: US 8,763,605 B2
(45) Date of Patent: Jul. 1, 2014

(54) INHALATION DEVICE

(75) Inventors: Andrew Jones, Roslindale, MA (US);
Richard L. Miller, Needham, MA (US)

(73) Assignee: Manta Devices, LLC, Roslindale, MA (US)

( * ) Notice: Subject to any disclaimer, the term of this patent is extended or adjusted under 35 U.S.C. 154(b) by 1768 days.

(21) Appl. No.: 11/491,004

(22) Filed: Jul. 20, 2006

(65) Prior Publication Data
US 2007/0151562 A1    Jul. 5, 2007

Related U.S. Application Data

(60) Provisional application No. 60/734,575, filed on Nov. 8, 2005, provisional application No. 60/703,032, filed on Jul. 27, 2005, provisional application No. 60/700,947, filed on Jul. 20, 2005.

(51) Int. Cl.
A61M 15/00    (2006.01)
A61M 11/00    (2006.01)
A61M 11/02    (2006.01)

(52) U.S. Cl.
CPC ........... *A61M 15/0045* (2013.01); *A61M 11/02* (2013.01); *A61M 15/0038* (2014.02); *A61M 15/001* (2014.02); *A61M 15/0048* (2014.02); *A61M 2202/064* (2013.01); *A61M 15/0043* (2014.02); *A61M 15/0065* (2013.01); *A61M 15/0085* (2013.01); *A61M 2205/07* (2013.01); *A61M 15/0028* (2013.01); *A61M 15/0003* (2014.02)
USPC ................................. 128/203.15; 128/203.21

(58) Field of Classification Search
CPC ............ A61M 11/02; A61M 15/0045; A61M 15/0028; A61M 15/0065; A61M 15/0043; A61M 15/0048; A61M 15/0003; A61M 15/0038; A61M 2202/064; A61M 2205/07

USPC ............ 128/200.14, 200.16, 200.17, 203.12, 128/203.15, 203.21, 204.13; 222/80, 83, 222/83.5, 85, 87, 90
See application file for complete search history.

(56) References Cited

U.S. PATENT DOCUMENTS 2,307,986 A   1/1943   Bolte et al.
2,860,638 A   11/1958  Bartolomeo
(Continued)

FOREIGN PATENT DOCUMENTS

DE    4400083 A1    7/1995
EP    0407276       1/1991
(Continued)

*Primary Examiner* — Justine Yu
*Assistant Examiner* — Douglas Sul
(74) *Attorney, Agent, or Firm* — Wolf, Greenfield & Sacks, P.C.

(57) ABSTRACT

The present invention provides for the integration of drug dispersion methods into a drug or medicine delivery system. The drug dispersion methods used include shear (e.g., air across a drug, with or without a gas assist), capillary flow or a venturi effect, mechanical means such as spinning, vibration, or impaction, and turbulence (e.g., using mesh screens, or restrictions in the air path). These methods of drug dispersion allow for all of the drug in the system to be released, allowing control of the dosage size. These methods also provide for drug metering, fluidization, entrainment, deaggragation and deagglomeration. The present invention also provides for the integration of a drug sealing system into the device. The drug sealing system provides a way of blocking the migration of drug from one area of the package to another. The drug seal system can also provide a method of tightly containing the drug until the package is opened, of directing airflow through the package and of managing and containing the drug during the package/device manufacturing process.

12 Claims, 14 Drawing Sheets

(56) References Cited

U.S. PATENT DOCUMENTS

| | | | |
|---|---|---|---|
| 2,974,787 A | 3/1961 | Cooper | |
| 3,888,253 A | 6/1975 | Watt et al. | |
| 2,893,392 A | 6/1976 | Gerstel et al. | |
| 4,338,931 A | 7/1982 | Cavazza | |
| 4,601,896 A | 7/1986 | Nugent | |
| 4,991,605 A * | 2/1991 | Keritsis | 131/335 |
| 5,035,237 A | 7/1991 | Newell et al. | |
| 5,167,242 A | 12/1992 | Turner et al. | |
| 5,320,714 A * | 6/1994 | Brendel | 128/203.15 |
| 5,388,572 A | 2/1995 | Mulhauser et al. | |
| 5,400,808 A | 3/1995 | Turner et al. | |
| 5,476,093 A | 12/1995 | Lankinen | |
| 5,501,236 A | 3/1996 | Hill et al. | |
| 5,562,918 A | 10/1996 | Stimpson | |
| 5,622,166 A | 4/1997 | Eisele et al. | |
| 5,669,378 A | 9/1997 | Pera et al. | |
| 5,673,793 A | 10/1997 | Seidler | |
| 5,893,452 A | 4/1999 | De Nervo | |
| 5,921,237 A | 7/1999 | Eisele et al. | |
| 5,954,204 A | 9/1999 | Grabowski | |
| 6,029,663 A | 2/2000 | Eisele et al. | |
| 6,089,228 A | 7/2000 | Smith et al. | |
| 6,209,538 B1 | 4/2001 | Casper et al. | |
| 6,328,034 B1 | 12/2001 | Eisele et al. | |
| 6,401,712 B1 | 6/2002 | Von Schuckmann | |
| 6,427,688 B1 * | 8/2002 | Ligotke et al. | 128/203.15 |
| 6,443,152 B1 | 9/2002 | Lockhart et al. | |
| 6,443,307 B1 | 9/2002 | Burridge | |
| 6,550,477 B1 | 4/2003 | Casper et al. | |
| 6,595,210 B2 * | 7/2003 | Ohki et al. | 128/203.15 |
| 6,655,381 B2 | 12/2003 | Keane et al. | |
| 6,679,256 B2 * | 1/2004 | Ingle et al. | 128/203.21 |
| 6,810,872 B1 | 11/2004 | Ohki et al. | |
| 6,941,947 B2 | 9/2005 | Young et al. | |
| 6,971,384 B2 | 12/2005 | Gieschen et al. | |
| 7,025,056 B2 | 4/2006 | Eason et al. | |
| 7,025,057 B2 | 4/2006 | Chawla | |
| 7,143,765 B2 | 12/2006 | Asking et al. | |
| 7,401,713 B2 | 7/2008 | Ede et al. | |
| 7,588,030 B2 * | 9/2009 | Ede et al. | 128/203.21 |
| 7,617,822 B2 | 11/2009 | De Boer et al. | |
| 2001/0029948 A1 | 10/2001 | Ingle et al. | |
| 2002/0006316 A1 | 1/2002 | Schuler et al. | |
| 2002/0020408 A1 | 2/2002 | Knauer | |
| 2002/0092523 A1 | 7/2002 | Connelly et al. | |
| 2003/0034271 A1 | 2/2003 | Burridge | |
| 2004/0206350 A1 * | 10/2004 | Alston et al. | 128/203.12 |
| 2004/0236282 A1 | 11/2004 | Braithwaite | |
| 2005/0022813 A1 | 2/2005 | Alston | |
| 2006/0108877 A1 | 5/2006 | Tegel | |
| 2006/0157053 A1 * | 7/2006 | Barney et al. | 128/200.23 |
| 2006/0169278 A1 | 8/2006 | Djupesland et al. | |
| 2007/0023381 A1 | 2/2007 | Cerveny | |
| 2007/0074721 A1 | 4/2007 | Harmer et al. | |
| 2008/0314384 A1 | 12/2008 | Harris et al. | |
| 2009/0250057 A1 | 10/2009 | Wachtel | |

FOREIGN PATENT DOCUMENTS

| | | |
|---|---|---|
| GB | 1211168 A | 11/1967 |
| GB | 2179260 | 3/1987 |
| GB | 2405798 | 3/2005 |
| GB | 2405798 A | 3/2005 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO 01/85097 | 11/2001 |
| WO | WO 02/098495 A1 | 12/2002 |
| WO | WO 03/000326 A1 | 1/2003 |
| WO | WO 03/015857 A1 | 2/2003 |
| WO | WO 2005/002654 A3 | 1/2005 |
| WO | WO 2005/025656 A1 | 3/2005 |
| WO | WO 2005/030305 A1 | 4/2005 |

* cited by examiner

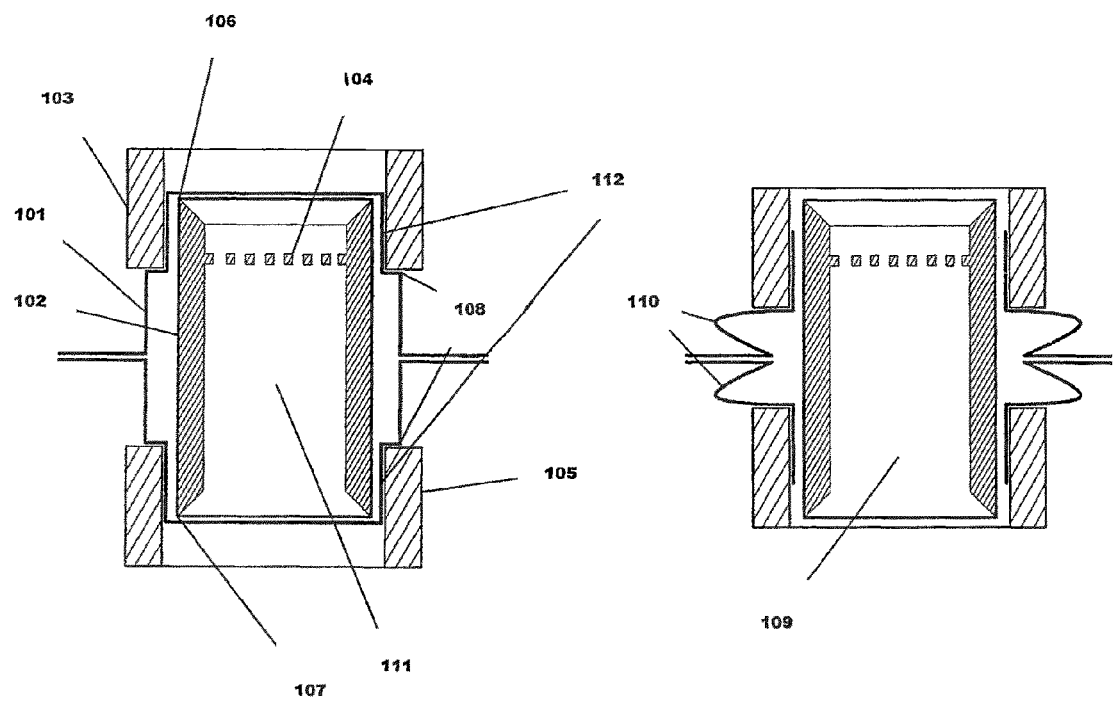
Figure 1A                    Figure 1B

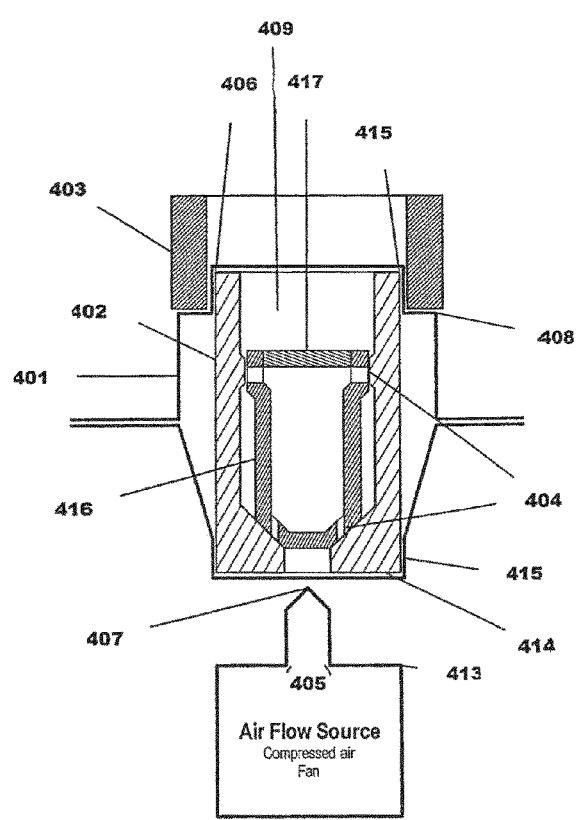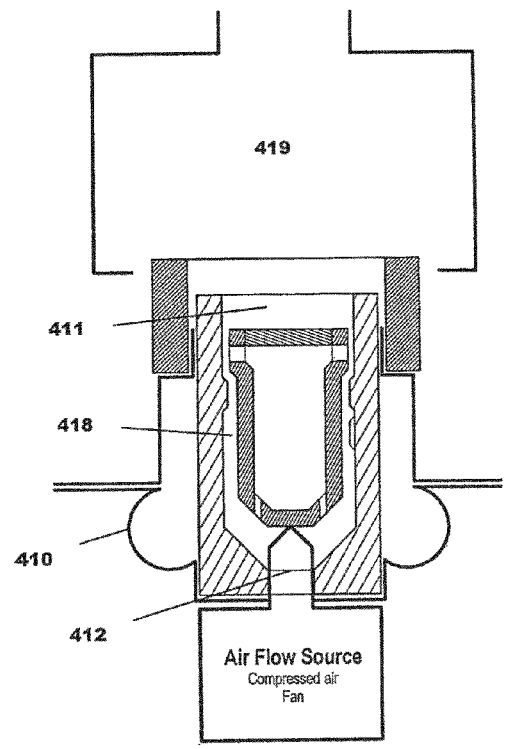
Figure 4A                    Figure 4B

INHALATION DEVICE

RELATED APPLICATIONS

This application claims the benefit under 35 U.S.C. 119(e) of the following U.S. Provisional Applications: Ser. No. 60/734,575, filed Nov. 8, 2005; Ser. No. 60/703,032 filed Jul. 27, 2005; and Ser. No. 60/700,947 filed Jul. 20, 2005, each of which is entitled "INHALATION DEVICE."

BACKGROUND OF THE INVENTION

The present invention relates to a system for storing and delivering substances, such as medicines. The present invention is particularly useful for the administration of medicine by inhalation.

Various drugs in dry powder form may be inhaled directly into the lungs through the mouth or nose. Inhalation allows the drug to bypass the digestive system and may eliminate the need for other more invasive drug application techniques, such as hypodermic injections. Direct inhalation can also allow smaller doses of a drug to be used to achieve the same desired results as the same drug taken orally. Inhalation can also help avoid certain undesirable side effects associated with taking a medicine orally or by injection.

One form of delivery device that is employed for inhaling a drug is the pressurized aerosol or metered dose inhaler (MDI). MDI's are, however, not suitable for use by all patients, e.g., small children, or for the administration of all medicaments. In addition, MDI's use propellants that can cause environmental damage. A widely used alternative is the so-called dry powder inhaler in which medicament powder is dispensed from an elongate gelatin capsule by causing the capsule to rotate and/or vibrate in an airstream, releasing the medicament that is inhaled by the patient. The capsules may be pierced by a suitable puncturing mechanism to release the medicament, or the capsules may be supplied in pre-pierced form. Additional packaging that prevents loss of powder from the capsule and the ingress of moisture is often necessary.

Gelatin capsules, and known drug delivery devices for inhalation, suffer from numerous disadvantages. For example, gelatin capsules are not impervious to moisture so exposure to the atmosphere can result in absorption of moisture. This may lead to agglomeration of the medicament powder particles. These problems may be particularly acute where, as is often the case, the medicament is hygroscopic. As a result, capsules must be packaged in secondary packaging such as a blister package, which significantly increases the overall bulk of the device.

In addition, the secondary packaging can be unwieldy or difficult to open, particularly in an emergency situation where the medicine must be delivered as fast as possible under stressful circumstances.

Another disadvantage with the gelatin capsules is that they may become brittle. In this case, the piercing operation may produce shards or fragments that can be inhaled by the patient. In addition, gelatin is a material of biological origin and therefore often contains a certain amount of microbiological organisms, leading to possible contamination of the medicament.

Removal of the capsule from the secondary packaging and loading it into the device may require a degree of dexterity greater than that possessed by some patients. In addition, the motion of the elongate gelatin capsule within the device may be irregular, leading to incomplete or variable dispensing of the powdered medicament.

Other dry powder inhaler systems use foil based drug storage configurations. These systems also suffer from a variety of disadvantages. Many foil-based systems require complex manufacturing and filling processes. In addition, to open these foil based systems, external puncturing mechanisms, which can cause "dead spots" of trapped medication, are normally used.

SUMMARY OF THE INVENTION

The present invention meets the foregoing objects by providing a sealed device for storing and delivering a substance, such as a medicine. The system and method for storing and delivering a medicine into an air path includes a first chamber that constrains the medicine to a particular area. Part of the first chamber defines at least one boundary of the air path. The air path is originally sealed but is capable of being opened by a first opening device that is capable of opening at least one air passage into the air path. This allows dispersion of said medicine into said air path. The system further includes a dose metering system that is integral with the first chamber. The dose metering system may be located inside the first chamber or it may be part of the wall of the first chamber. In some aspects of the invention, the dose metering system may include an air deflection system.

The system may have a moisture impermeable barrier that at least partially seals the air path. The first opening device, a second opening device or a combination thereof may be used to open an air passage into the air path. Penetration of the moisture impermeable barrier, or movement of another part of the system that seals the air path provides the requisite opening. In some embodiments, the first opening device is internal to the first chamber. A preferred second opening device is a plunger which may have a cutting edge.

The system may also have a second chamber interior to the first chamber. This second chamber may contain the medicine and this second chamber may be movable relative to the first chamber. For example, the second chamber may be movable from a first position to a second position by the action of a second opening device like a plunger. The second chamber may include access holes that allow dispersion of the medicine into the air path when the second chamber has moved to the second position. Preferably, the second chamber is constructed such that the access holes are blocked to prevent release of the medicine into the air path when the second chamber is in the first position but the access holes are opened when the second chamber is moved to the second position.

The system may also include an obstacle that delineates at least a portion of the air path in conjunction with at least one wall of the first chamber. The obstacle may form part of a wall of the second chamber.

The system may include an active method of assisting in dispersing the medicine into the air path. One active way of assisting in the dispersion is a source of active air flow to assist in dispersing the medicine into the air path. Preferred sources of active air flow are a fan and a source of compressed air. When using the active air flow source, the system may include a mixing chamber, preferably one made of a flexible material. Alternatively, the system may also include a source of vibration to assist in dispersing the medicine into the air path. The vibration source can cause the second chamber to tumble.

The present invention provides for the integration of drug or medicine dispersion methods into the medicine delivery system. The dispersion methods used include shear (e.g., air across a drug, with or without a gas assist), capillary flow or a venturi effect, m tion, or impaction, and turbulence (e.g., using mesh screens, or restrictions in the air path). These methods of drug dispersion allow for all of the drug in the packaging device to be released, allowing control of the dosage size. These methods also provide for drug metering, fluidization, entrainment, deaggragation and deagglomeration.

The present invention also provides for the integration of a drug sealing system into the medicine delivery system. The drug sealing system provides a method of blocking the migration of drug from one area of the package to another. The drug sealing system can also provide a way of tightly containing the drug until the air path in the system is opened, of directing airflow through the package and of managing and containing drug during the manufacturing process.

All of the design embodiments of the medicine delivery system can be configured for passive or active applications. In particular, variants can be made on each of the designs that use compressed air, vibration, spinning or the like to assist in dispersing the drug. The disclosed drug package can be integrated into a wide variety of inhaler configurations including a single-dose and multi-dose applications in either active or passive design format. In addition, the concepts described could also be applied to combination dose configurations and therapies.

BRIEF DESCRIPTION OF THE DRAWING

FIGS. 1A and 1B illustrate a basic variant of the drug or medicine delivery system of the invention having a sealed air path and a screen or mesh for drug dispersion in open and closed position;

FIGS. 4A and 4B illustrate a drug delivery system similar to that of FIGS. 3A and 3B except it includes an active air supply that assists in drug dispersion;

DETAILED DESCRIPTION OF THE INVENTION

Figures 2A, 2B:
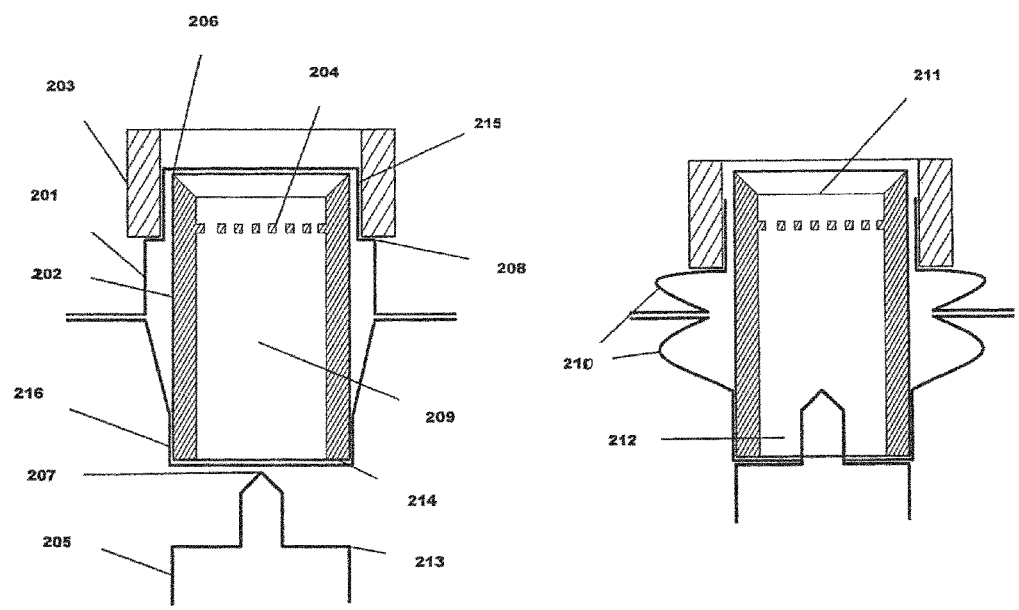
FIGS. 2A and 2B illustrate a drug delivery system such as is shown in FIGS. 1A and 1B in open and closed position but with the addition of a plunger that pierces the seal and activates the internal opening mechanism.
Figures 3A, 3B:
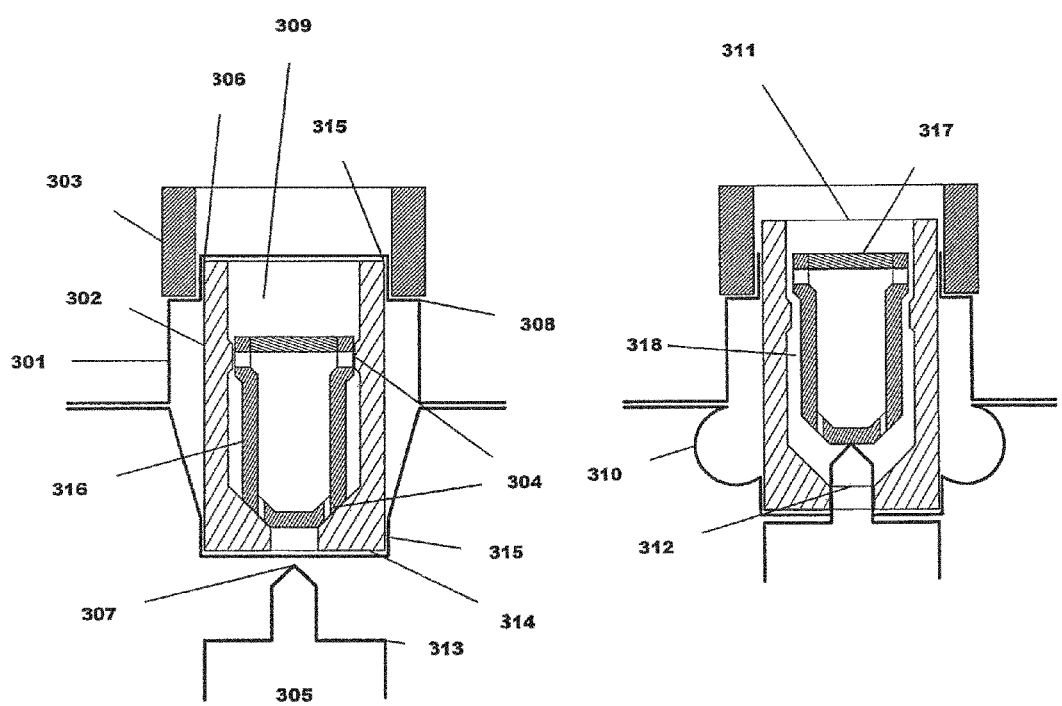
FIGS. 3A and 3B illustrate a drug delivery system with a second chamber in an open and closed position that allows for a venturi effect to assist in drug dispersion.

The medicine storage and delivery system of the present invention provides an improved package for storing and delivering a medicine. The enhanced sealing of the device promotes improved delivery of the medicine by providing better protection of the medicine from the elements, particularly if it is in the form of a powder, and improved opening of the packaging to eliminate "dead spots." In addition, the present invention provides active and passive variants that allow for better drug dispersion and improved delivery capabilities.

The following definitions are used throughout the specification and the claims:

The term "puncturing" refers to any form of opening, including piercing, perforating, peeling and tearing.

The term "internal opening mechanism" or "IOM" refers to a device that is used to puncture or open at least one portion of a sealed device. The IOM can take many forms including a tube shape with an annular cutter at each end, or a sliding internal chamber with a piercing end. The internal opening mechanism can act as a structural support to minimize deformation of the drug package by an external opening device.

The term "drug seal system" "DSS" refers to a component or interaction between components that provide a means of blocking the migration of drug from one area of the package to another. The drug seal system can also provide a means of tightly containing the drug until the package is opened, a means of directing airflow through the package and a means of managing and containing drug during the package/device manufacturing process. The drug sealing system can vary from a chamber to a flat cover depending on the package requirements. The DSS can also provide a cutting edge for opening the air path, and can be located inside or outside a moisture barrier. In embodiments where the DSS is located outside the moisture barrier, it could be a part of the inhaler device or a separate piece.

The term "dose metering system" or "DMS" refers to a dedicated component, a specific geometry associated with a component, or the interaction between two or more components, that is designed to facilitate drug fluidization and dispersion along the air path through the drug package. The DMS can be integrated into the internal opening mechanism, the moisture barrier, the air path, the drug sealing system or in combination with any of these components, or can be a stand alone component. The DMS can be activated by actuation of the IOM or DSS, can have a stationary geometry or be a movable component, can be passive or active, and can utilize aerodynamics, compressed air, vibration or centrifugal force.

The term "external plunger" or "plunger" refers to a movable component that is designed an air passage into the air path to open. The external plunger can be designed to pierce the seal of the air path from the outside by means of a cutting protuberance or can be designed to press the moisture barrier against an internal cutting protuberance located on the IOM, DSS, DMS or combination of these. The external plunger minimizes the space required to open the package, can activate the simultaneous opening of the air path by the IOM and drug sealing system (if applicable) and DMS (if applicable), and can act as a drug seal in some embodiments. Furthermore, the external plunger can be designed to provide the air inlet into the drug package, through the plunger. Air channels integrated into the plunger can direct airflow in a manner critical to emptying drug from the package.

The term "active" refers to use of an external mechanism or force in addition to the patient's respiration.

The term "passive" refers to the use of the patient's respiration alone.

The term "chamber" refers to an area of the system that includes a portion that encloses a specific area. Chambers can be a number of shapes depending on the desired fluid dynamic interaction with the airflow. Chamber walls can include channels that direct or divert airflow through or around the inside or outside of the chamber. Chambers can vary in shape from one portion of the chamber to another. Chambers can be movable or stationary.

The term "reservoir" is a storage area for holding drug. Reservoirs can have opening(s) that include a shaped geometry that is optimized to direct or divert the flow of air from the air path into, around or through the reservoir. The shaped geometry can also facilitate powder fluidization, entrainment, dispersion and deaggregation/deagglomeration. Openings can be symmetrical or asymmetrical and oriented perpendicular, parallel or at some angle to the airflow.

The invention is best described in conjunction with the following Figures.

FIGS. 1A and 1B show a basic variant of the drug delivery system of the invention. FIG. 1A shows the device in the closed position and FIG. 1B shows it in the open position. The drug delivery system includes moisture barrier 101, internal opening mechanism 102, outlet ring 103 (with integral drug sealing system), and dose metering system 104.

Moisture barrier 101 is comprised of two layers of a moisture impervious material, typically a plastic coated foil. The top and bottom layers of foil are pre-formed to create moisture barrier 101 when attached together. Furthermore, the top and bottom layers have a formed step 108 that interfaces with outlet ring 103. Internal opening mechanism 102 resides within moisture barrier 101 and is integral with first chamber 111. The drug dose resides inside first chamber 111.

First chamber 111 has an air inlet opening and an air outlet opening, which are in close proximity with the moisture barrier 101 when the package is assembled. First cutting edge 106 and second cutting edge 107 are located proximate to first and second openings in first chamber 111. The dose sealing system consists of outlet ring 103 and base 105. The dose sealing system provides an annular pressure creating a tight seal 112 between internal opening mechanism 102 and moisture barrier 101 at both of the first chamber 111 openings.

A dose metering system in the form of a mesh screen 104 is integrated into the first chamber 111.

To open the package and release the drug, pressure is applied to base 105, causing base 105 to move toward outer ring 103. This action applies pressure on the formed steps 108 in moisture barrier 101, causing moisture barrier 101 to slide against internal opening mechanism 102, which pierces moisture barrier at the first and second cutting edge. This opens an air path 109 through first chamber 111. The foil layers of moisture barrier 101 deform 110 to allow the relative movement of base 105 and outer ring 103.

Air can be drawn through the open first chamber 111, entraining drug into the air stream. Dose metering system 104 prevents the powder from leaving the package as one large clump and helps fluidize the dose.

FIG. 2 illustrates a drug delivery device substantially similar to that of FIG. 1 except that the inlet side of the moisture barrier is pierced with an external piercing device integrated into a plunger.

Moisture barrier 201 is comprised of two layers of a moisture impervious material, typically a plastic coated foil. The top and bottom layers of foil are pre-formed to create moisture barrier 201 when attached together. Furthermore, the top layer has a formed step 208 that interfaces with outlet ring 203. Internal opening mechanism 202 resides within moisture barrier 201 and is integral with first chamber 209. The drug dose resides inside first chamber 209.

First chamber 209 has multiple openings including air inlet 212 and outlet 211, which are in close proximity with the moisture barrier 201 when the package is assembled. There is a first cutting edge 206 at the outlet opening 211 in first chamber 209 and a second cutting edge 207 integrated into a protuberance on the plunger 205.

The dose sealing system consists of the outlet ring 203, which provides annular pressure creating a tight seal 215 between internal opening mechanism 202 and moisture barrier 201 at first chamber outlet opening 211. In this embodiment, the dose sealing system includes external annular ring (not shown) or interference fit 216 between moisture barrier 201 and internal opening mechanism 202.

Integrated into first chamber 209 is a dose metering system in the form of a screen 204.

To open the package, plunger 205 is moved toward outlet ring 203, which causes the plunger protuberance 207 to pierce moisture barrier 201 at inlet opening 212 proximate to first chamber 209. The plunger protuberance moves into first chamber 209 until the plunger shoulder 213 contacts the internal opening mechanism 202 at the inlet opening edge 214. As plunger 205 continues to move towards outlet ring 203, the internal opening mechanism slides against moisture barrier 201, causing first cutting edge 206 to protrude through moisture barrier 201 at outlet opening 211. Moisture barrier 201 deforms 210 to allow the relative movement of plunger 205 and outlet ring 203.

Air can be drawn through the open first chamber 209, possibly through plunger 205, entraining drug into the air stream. Drug metering system 204 prevents the drug from leaving the package as one large clump and helps fluidize the dose.

In alternate configurations, the drug metering system may be outside of the first chamber, or may not be present in the package.

The drug delivery device shown in FIGS. 1 and 2 can readily be used in active configurations such as spinning, vibration and forced airflow source. Spinning the drug delivery device about its long axis would serve the purpose of spreading the drug out against the first chamber walls, creating a large dose surface area to facilitate rapid metered fluidization. Similarly, vibration from an "Active" source would facilitate drug dispersion. The active vibration source could be a piezo-electric actuator or a motor. The active configuration alternatively could use an active air flow source such as compressed air or a fan. In this case, the entrained dose would likely be captured in a mixing chamber before being delivered to the patient. The mixing chamber could be a rigid vessel or a flexible design that inflates during use and collapses for storage.

FIG. 3 illustrates a device similar to that shown in FIG. 2 except that a second chamber has been added to store the drug dose. The second chamber provides benefits including secure containment of the drug dose, ease of manufacturing and drug filling, and drug metering. The second chamber can move relative to the first chamber and has an open and closed position. To open the package, plunger 305 pierces the moisture barrier and pushes against the second chamber causing it to slide from the closed position to the open position. Air flows through the plunger, around and through the second chamber and out the other side of the moisture barrier. Drug is entrained into the air path by venturi effect through openings in the second chamber. The airflow through and around the second chamber is managed by air channels formed by the first chamber and the second chamber. The air channels are shaped to create a restriction at the second chamber openings, increasing the air velocity, and creating the venturi effect.

Moisture barrier 301 is formed of two layers of a moisture impervious material, typically a plastic coated foil. The top and bottom layers of foil are pre-formed to create moisture barrier 301 when attached together. One layer has a formed step 308 that interfaces with outlet ring 303.

Internal opening mechanism 302 resides within moisture barrier 301 and creates first chamber 309. First chamber 309 has openings for air inlet 312 and outlet 311. Inlet 312 and outlet 311 are in close proximity with the moisture barrier 301 when the package is assembled. There is a first cutting edge 306 at outlet opening 311 in first chamber 309 and second cutting edge 307 integrated into a protuberance on plunger 305.

Second chamber 316 resides within first chamber 309 and contains the drug dose. Second chamber has a drug sealing system with openings 304 that are covered by interference with the internal opening mechanism 302 when the device is stored in its closed position. Second chamber 316 can be moved relative to first chamber 309 to eliminate the interference at the openings 304 to create a path between the first and second chambers. Integrated into second chamber 316 is a drug metering system in the form of one or more openings designed to fluidize powder in second chamber 316 and facilitate dose entrainment into the air path through first chamber 309 by venturi effect. Second chamber plug 317 is used to close an opening after filling second chamber 316 with drug during manufacturing.

Air channels 318 direct airflow past second chamber openings 304 and through the device and are formed into the first chamber 309 and the walls of second chamber 316. These air channels 318 could also take the form of a nozzle or orifice.

To open the device and release the drug, plunger 305 and outlet ring 303 are moved together, causing the protuberance on plunger 305 to pierce moisture barrier 301 at inlet opening 312 to first chamber 309. The protuberance on plunger 305 moves into first chamber 309 until plunger 305 contacts second chamber 316, causing it to open by movement from the closed to open position. The protuberance on plunger 305 continues to move into first chamber 309 until plunger shoulder 313 contacts internal opening mechanism 302 at the inlet opening edge 314. As plunger 305 continues to move towards outlet ring 303, internal opening mechanism 302 slides against moisture barrier 301, causing first cutting edge 306 to protrude through moisture barrier 301 at outlet opening 311. Moisture barrier 301 deforms 310 to allow the relative movement of plunger 305 and outlet ring 303.

Air can be drawn through the open first chamber 309, possibly through plunger 305, and around and through second chamber 316 to entrain drug into the air stream. Dose metering system 304, embodied by specific opening geometry in second chamber 316, prevents the drug from leaving the package as one large clump and helps fluidize the dose.

This design could also be applied in a combination dose configuration where multiple drugs are delivered to the patient at the same time. Typically, the drugs need to be stored separately from each other and then combined at the time of inhalation. This can be accomplished by dividing second chamber 316 into multiple cavities, or by including multiple second chambers 316 within the device.

FIG. 4 illustrates a device similar to that shown in FIG. 3, except that the inhaler relies on an “Active” source for the air movement through the inhaler instead of the patient’s inhaling capability. To ensure proper mixing and aerosolization, it is envisioned that the entrained dose may be captured in a mixing chamber 419 before being delivered to the user. A mixing chamber may be required if the active air source is at a higher pressure or flow rate than would want to be delivered directly to the user. The active airflow source could be compressed air or a fan. The mixing chamber could be a rigid vessel or a flexible design that inflates during use and collapses for storage. The airflow may be through, or around, plunger 405. The other parts shown in FIG. 4 are similar to those shown in FIG. 3.

This design could also be applied in a combination dose configuration where multiple drugs are delivered to the patient at the same time.

FIG. 5 illustrates a device similar that shown in FIG. 3 except that second chamber 516 is designed to vibrate to assist in dose metering and evacuation. Second chamber 516 provides benefits including secure containment of the drug dose, ease of manufacturing and drug filling, and drug metering. Second chamber 516 can move relative to the first chamber 509. To open the package, plunger 505 pierces moisture barrier 501 and pushes against second chamber 516, causing it to slide from the closed position to the open position. Air flows through plunger 505, around and through second chamber 516 and out the other side of first chamber 509. Powder is entrained into the air path by vibration caused by the movement of air around second chamber 516. The airflow through and around second chamber 516 is controlled by air channels formed by the internal opening mechanism 502 and second chamber 516. Second chamber 516 may be held in position by a protruding tether that is in contact with internal opening mechanism 502.

Moisture barrier 501 is comprised of two layers of a moisture impervious material, typically a plastic coated foil. The top and bottom layers of foil are pre-formed to create moisture barrier 501 when attached together. Furthermore, the top layer has a formed step 508 that interfaces with outlet ring 503. Internal opening mechanism 502 resides in moisture barrier 501 and creates first chamber 509.

First chamber 509 has openings for air inlet 512 and outlet 511, which are in close proximity to moisture barrier 501 when the device is assembled. There is a first cutting edge 506 at outlet opening 511 in first chamber 509 and a second cutting edge 507 integrated into a protuberance on plunger 505.

Second chamber 516 resides within first chamber 509 and contains the drug dose. Second chamber 516 contains a drug sealing system including openings 504 that are covered by interference fit with the first chamber 5099 when the device is in its closed position. Second chamber 516 can be moved relative to first chamber 509 to eliminate the interference at openings 504 to open the device and create a path between the first and second chambers.

Also integrated into second chamber 516 is a drug metering system in the form of one or more openings designed to fluidize powder in second chamber 516 and facilitate drug entrainment by vibration and venturi effect into the air path through first chamber 509. Second chamber 516 has a protruding section 519 extending toward air path inlet 512 that attaches to the internal opening mechanism 502. Protruding portion or geometry 519 is the only point of contact with the internal opening mechanism 502 when second chamber 516 is in the open position. Protruding geometry 519 is shaped to allow second chamber 516 to vibrate in response to surrounding airflow turbulence. For example, protruding geometry 519 may be a flexible beam (like a tuning fork tine) or a flexible tether (such as a string or chain). Second chamber plug 517 is used to close an opening after filling second chamber 516 with drug during manufacturing.

To open the device and release the drug, plunger 505 and outlet ring 503 are moved together; causing protuberance 507 on plunger 505 to pierce moisture barrier 501 at the inlet opening 512 to first chamber 509. Protuberance 507 on plunger 505 moves into first chamber 509 until plunger 505 contacts second chamber 516, causing it to open by movement from the closed to open position. Protuberance 507 on plunger 505 continues to move into first chamber 509 until plunger shoulder 513 contacts internal opening mechanism 502 at the inlet opening edge 514. As plunger 505 continues to move towards outlet ring 503, internal opening mechanism 502 slides against moisture barrier 501, causing cutting edge 506 to protrude through moisture barrier 501 at outlet opening 511. Moisture barrier 501 deforms 510 to allow the relative movement of plunger 505 and outlet ring 503.

Air can be drawn through the open first chamber 509, possibly through plunger 505, and goes around and through second chamber 516, causing second chamber 516 to vibrate, and entraining drug into the air stream. Dose metering system 504, formed by the specific opening geometry in second chamber 516, prevents the powder from leaving the package as one large clump and helps fluidize the dose.

This design could also be applied in a combination dose configuration where multiple drugs are delivered to the patient at the same time. Typically, the drugs need to be stored separately from each other and then combined at the time of inhalation. This can be accomplished by dividing second chamber 516 into multiple cavities, or by including multiple second chambers 516 within the device.

Figures 5A, 5B:
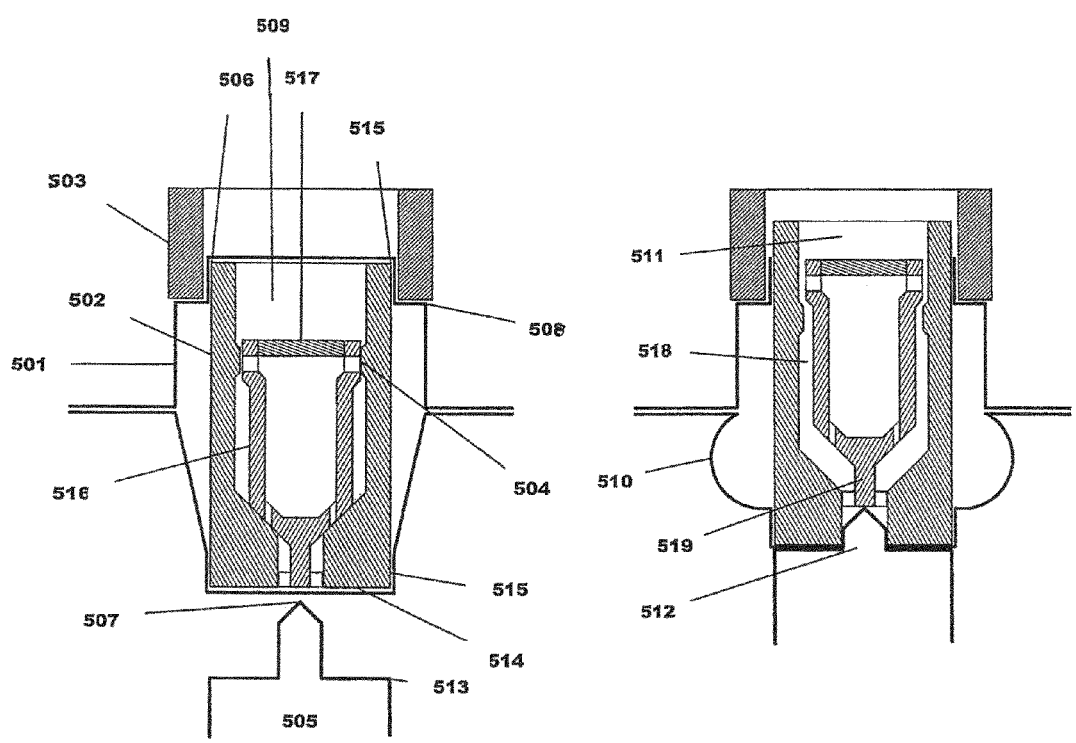
FIGS. 5A and 5B illustrate a drug delivery system similar to that of FIGS. 3A and 3B except it is designed to allow vibration to assist in drug dispersion.
Figures 6A, 6B:
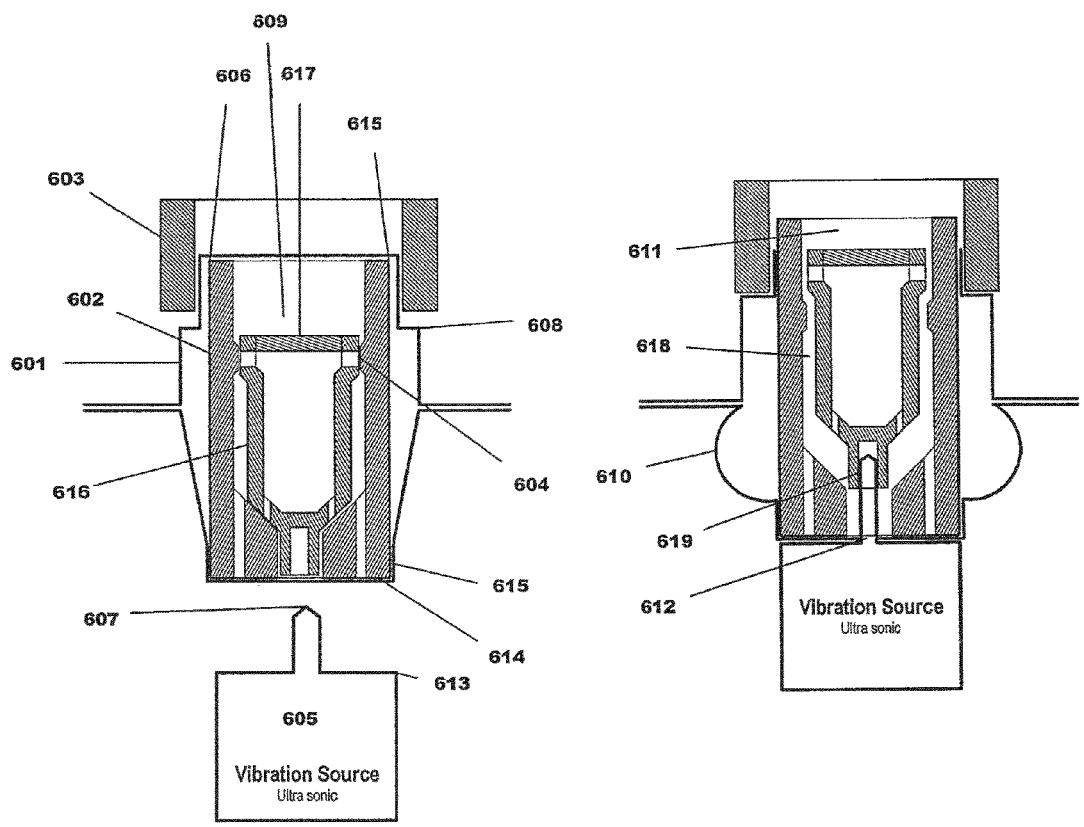
FIGS. 6A and 6B illustrate a drug delivery system similar to that of FIGS. 5A and 5B except it includes an active vibration source to assist in drug dispersion.

FIG. 6 is similar to the device described and illustrated in FIG. 5 except that the inhaler relies on an "Active" source for vibration of the drug dose chamber instead of the patient's inhaling capability to activate the system. The active vibration source could be a piezo-electric actuator or a motor, possibly integrated with plunger 605. The active vibration source can couple to second chamber 616 at the plunger interface, internal opening mechanism 602, or a combination of the two. An alternate configuration would be to locate the vibration source inside moisture barrier 601. The vibration source could be a piezoelectric material, a specific component geometry that can be excited at target frequencies and amplitudes, or a magnetically coupled resonance receiver. The internal vibration source could be an independent component or be fully or partially integrated into internal opening mechanism 602, moisture barrier 601, second chamber 616 or a combination thereof. Electro-mechanical coupling can be accomplished by means of plunger 605, which makes contact with the internal vibration source after piercing moisture barrier 601. An alternate coupling scheme would allow electro-mechanical contact once the internal vibration source moved outside moisture barrier 601 and contacted the device during package opening. Coupling can also be achieved by making a non-physical electrical or magnetic connection with the internal vibration source, such as through inductive coupling.

The active vibration configuration alternatively could use an active air flow source such as compressed air or a fan. In this case, the entrained dose would likely be captured in a mixing chamber (not shown) before being delivered to the patient. The mixing chamber could be a rigid vessel or a flexible design that inflates during use and collapses for storage. The active airflow through the package could be delivered through the plunger.

This design could also be applied in a combination dose configuration where multiple drugs are delivered to the patient at the same time.

FIG. 7 is similar to the device described in conjunction with FIG. 2 except that a second chamber has been added to store the drug dose. The second chamber provides benefits including secure containment of the drug dose, ease of manufacturing and drug filling, and drug metering into the air stream. The second chamber can move relative to the first chamber and has an open and closed position. To open the package, the plunger pierces the moisture barrier and pushes against the second chamber, causing it to slide from the closed position to the open position. Air may flow through the plunger, or around it, and possibly through the second chamber and out the other side of the moisture barrier. Powder exits through openings in the second chamber by a combination of tumbling, shaking and spinning, and is entrained into the air path. Powder may also exit the second chamber by venturi effect and/or by air flowing through the second chamber. The airflow around the second chamber may be managed by air channels formed by the first chamber. The air channels could be shaped to create a vortex or spinning of the air within the first chamber to facilitate tumbling and spinning of the second chamber.

Moisture barrier 701 is comprised of two layers of a moisture impervious material, typically a plastic coated foil. The top and bottom layers of foil are pre-formed to create moisture barrier 701 when attached together. The top layer has a formed step 708 that interfaces with matching outlet ring geometry 703.

An internal opening mechanism 702 resides in moisture barrier 701 and creates first chamber 709. First chamber 709 has openings for air inlet 712 and outlet 711, which are in close proximity with moisture barrier 701 when the device is assembled. There is a first cutting edge 706 at the outlet opening 711 in first chamber 709 and a second cutting edge 707 integrated into a protuberance on the plunger 705.

Second chamber 716 resides within first chamber 709 and contains the drug dose. Second chamber 716 has a drug sealing system 704 with the openings in second chamber being covered by interference fit with first chamber 709 when the device is in its closed position. Second chamber 716 can be moved relative to first chamber 709 internal opening mechanism 702 to eliminate the interference at the openings and create a path between the first and second chambers.

Integrated into the second chamber is a drug metering system in the form of one or more openings designed to fluidize powder in second chamber 716 and facilitate drug entrainment, primarily by tumbling and spinning, into the air path through first chamber 709. These openings can be at any location in second chamber 716 as required to obtain the desired functionality. Chamber plug 717 is used to close an opening in second chamber 716 after filling with drug during manufacturing.

To open the package, plunger 705 and outlet ring 703 are moved together, which causes the protuberance on the plunger to pierce moisture barrier 701 at the inlet opening 712 to first chamber 709. Protuberance 707 on plunger 705 moves into first chamber 709 until plunger 705 contacts second chamber 716 causing it to open by movement from the closed to open position. Protuberance 707 on plunger 705 continues to move into first chamber 709 until plunger shoulder 713 contacts the internal opening mechanism 702 at the inlet opening edge 714. As plunger 705 continues to move towards outlet ring 703, internal opening mechanism 702 slides against moisture barrier 701, causing cutting edge 706 to protrude through moisture barrier at outlet opening 711.

Moisture barrier deforms 710 to allow the relative movement of outlet ring 703 and internal opening mechanism 702.

Air can be drawn through the open first chamber 709, around and possibly through second chamber 716, tumbling or spinning second chamber 716 and entraining drug into the air stream. Mesh screen 719 restrains second chamber 716 within first chamber 709, and may also prevent the drug from leaving the package as one large clump.

This design could also be applied in a combination dose configuration where multiple drugs are delivered to the patient at the same time. Typically, the drugs need to be stored separately from each other and then combined at the time of inhalation. This can be accomplished by dividing second chamber 716 into multiple cavities, or by including multiple second chambers within the device.

Figures 7A, 7B:
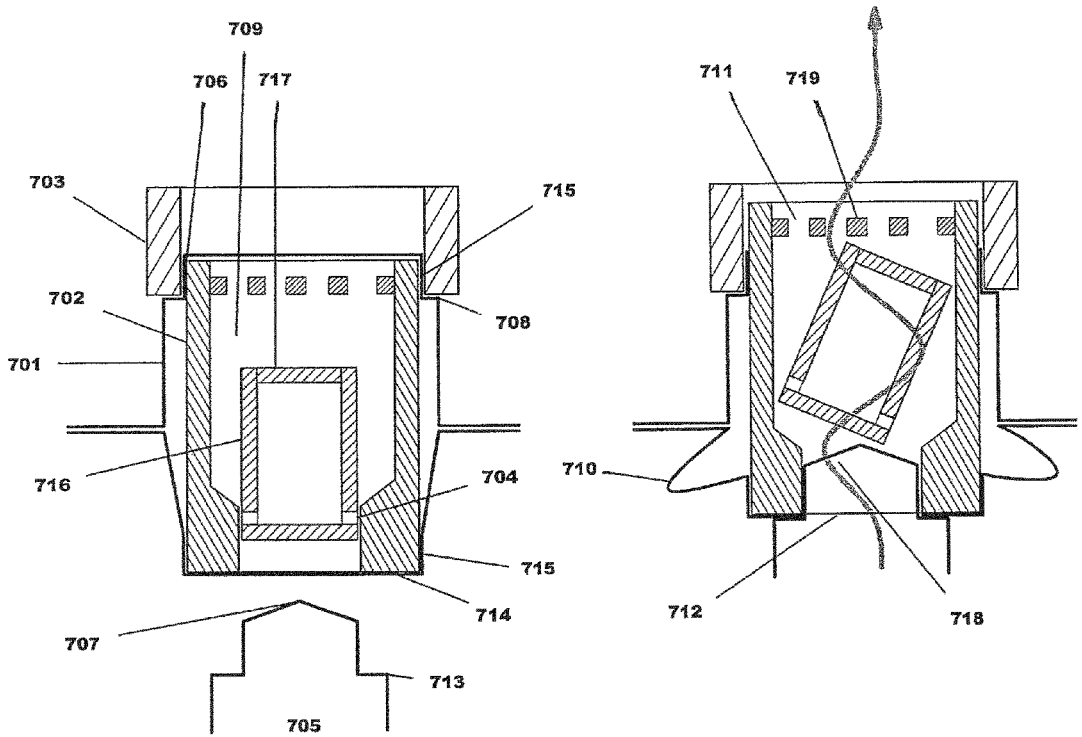
FIGS. 7A and 7B illustrate a drug delivery system with a second chamber in an open and closed position that allows for tumbling or shaking of the second chamber to assist in drug dispersion.
Figures 8A, 8B:
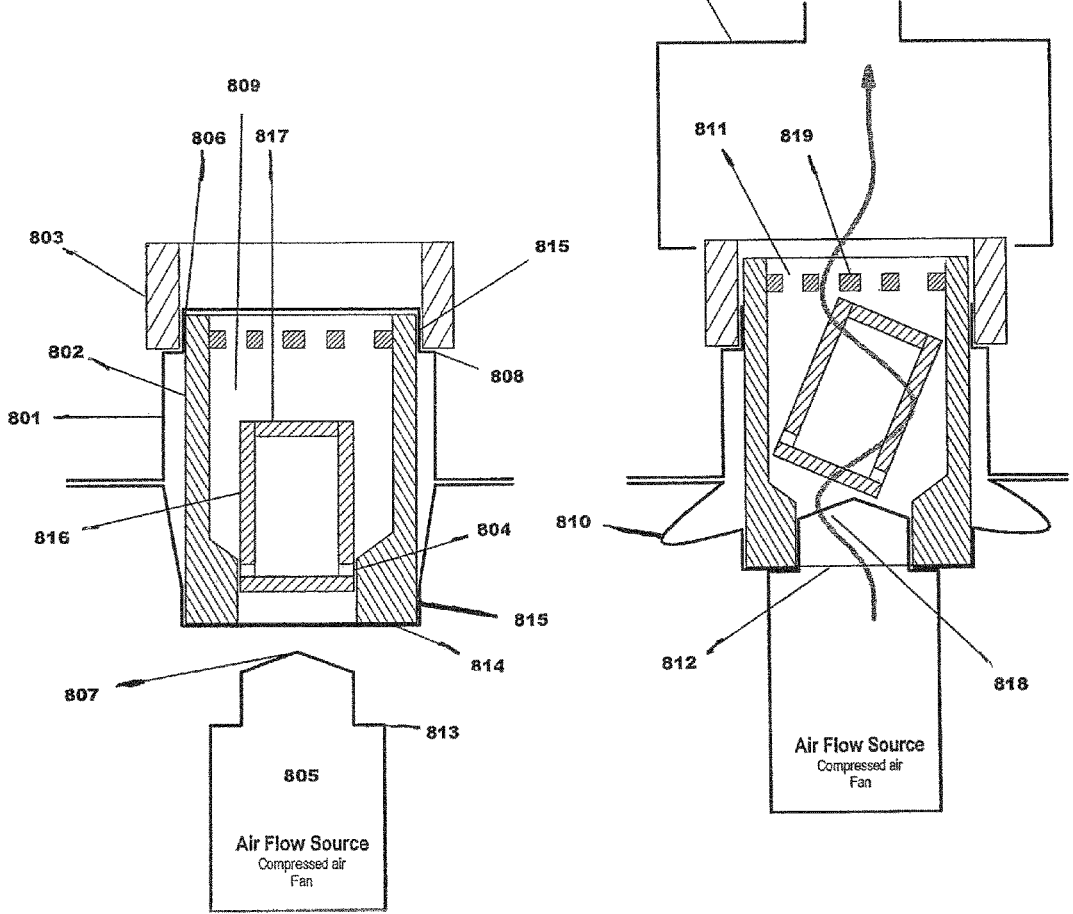
FIGS. 8A and 8B illustrate a drug delivery system similar to that of FIGS. 7A and 7B except it includes an active air flow source to assist in drug dispersion.

The tumbling chamber drug package configuration can also be utilized in an active inhaler system. FIG. 8 shows this configuration and its use is identical to that of FIG. 7, with the difference being that rather than relying on the patient's respiration for the air flow to create the tumbling action of second chamber 816, an active compressed air or impellor system could be used. This may be particularly helpful in cases where the patient's airflow rate capabilities are diminished due to medical conditions. Correspondingly, with an active airflow source, it is envisioned that the entrained dose could be captured in a mixing chamber 820 before being delivered to the user. The mixing chamber could be a rigid vessel or a flexible design that inflates during use and collapses for storage. The airflow through the device can be delivered through, or around, plunger 805.

This design could also be applied to a combination dose configuration where multiple drugs are delivered to the patient at the same time.

Figures 9A, 9B:
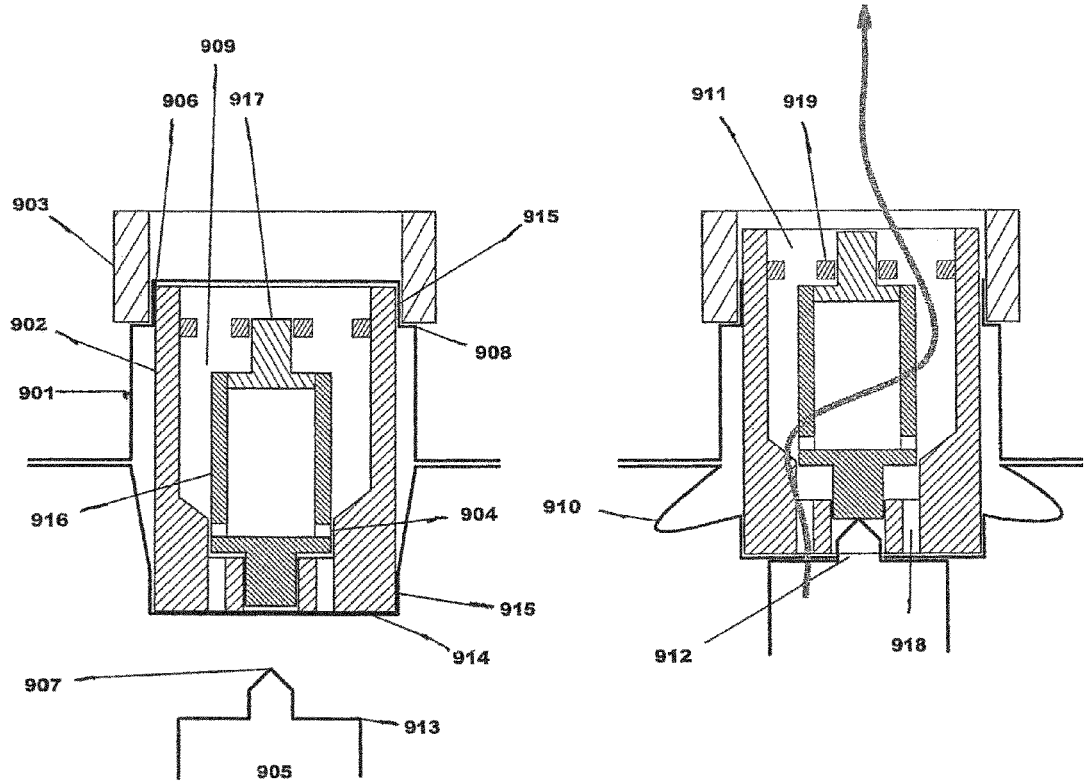
FIGS. 9A and 9B illustrate a drug delivery system with a second chamber in an open and closed position that allows for spinning of the third chamber to assist in drug dispersion.

FIG. 9 illustrates a device similar to the device of FIG. 2, except that a second chamber 916 has been added to store the drug dose. Second chamber 916 provides benefits including secure containment of the drug dose, ease of manufacturing and drug filling, and drug metering into the air stream. Second chamber 916 can move relative to internal opening mechanism 902. To open the device, plunger 905 pierces moisture barrier 901 and pushes against second chamber 916, causing it to slide from the closed position to the open position. Air may flow through plunger 905, and around and possibly through second chamber 916 and out the other side of moisture barrier. Powder exits through openings in second chamber 916 from the spinning action, and is entrained into the air path. Powder may also exit second chamber 916 by venturi effect and/or by air flowing through second chamber 916. The airflow around second chamber 916 may be directed or controlled by air channels formed by first chamber 909 internal opening mechanism 902. The air channels could be shaped to create a vortex or spinning of the air in first chamber 909 to facilitate spinning of second chamber 916.

Moisture barrier 901 is comprised of two layers of a moisture impervious material, typically a plastic coated foil. The top and bottom layers of foil are pre-formed to create moisture barrier 901 when attached together. Furthermore, the top layer has a formed step 908 that interfaces with the geometry of matching outlet ring 903.

Internal opening mechanism 902 resides within moisture barrier 901 and creates first chamber 909. First chamber 909 has openings for air inlet 912 and outlet 911, which are in close proximity with moisture barrier 901 when the device is assembled. There is a first cutting edge 906 at outlet opening 911 in first chamber 909 and a second cutting edge 907 integrated into a protuberance on the plunger 905.

Second chamber 916 resides within first chamber 909 and contains the drug dose. Second chamber 916 has a drug sealing system 904, with the openings in second chamber 916 being covered by an interference fit with internal opening mechanism 902 when the device is in its closed position. Second chamber 916 can be moved relative to internal opening mechanism 902 to eliminate the interference at the openings and create a path between the first and second chambers.

Integrated into second chamber is a drug metering system in the form of one or more openings designed to fluidize powder in second chamber 916 and facilitate drug entrainment, primarily by spinning, into the air path through first chamber 909. The openings can be in any location on second chamber 916. Chamber plug 917 is used to close an opening in second chamber 916 after filling with drug during manufacturing.

To open the device, plunger 905 is moved toward the outlet ring 903 which causes the cutting edge on the plunger protuberance to pierce moisture barrier 901 at inlet opening 912 to first chamber 909. The protuberance on plunger 905 moves into the first chamber 909 until plunger 905 contacts the second chamber 916 causing it to move from the closed to open position. The protuberance on plunger 905 continues to move into the first chamber 909 until plunger shoulder 913 contacts internal opening mechanism 902 at inlet opening edge 914. As plunger 905 continues to move towards outlet ring 903, internal opening mechanism 902 slides against moisture barrier 901, causing cutting edge 906 to protrude through moisture barrier 901 at the outlet opening 911. Moisture barrier deforms 910 to allow the relative movement of outlet ring 903 and internal opening mechanism 902.

Air can be drawn through the open first chamber 909, around and possibly through second chamber 916, spinning second chamber 916 and entraining drug into the air stream. Air inlets 918 can be configured to create a vortex within first chamber 909, which imparts a spinning action on second chamber 916. Second chamber 916 may have fins or other geometric details that are acted upon by the air to impart the spinning motion. Second chamber 916 is radially supported by first chamber 909 and a mesh screen 919 in order to guide the spinning motion. Mesh screen 919 also constrains second chamber 916 axially within first chamber 909, and may also prevent the drug from leaving the package as one large clump.

This design could also be applied in a combination dose configuration where multiple drugs are delivered to the patient at the same time. Typically, the drugs need to be stored separately from each other and then combined at the time of inhalation. This can be accomplished by dividing the second chamber 916 into multiple cavities, or by including multiple second chambers within the device.

Figures 10A, 10B:
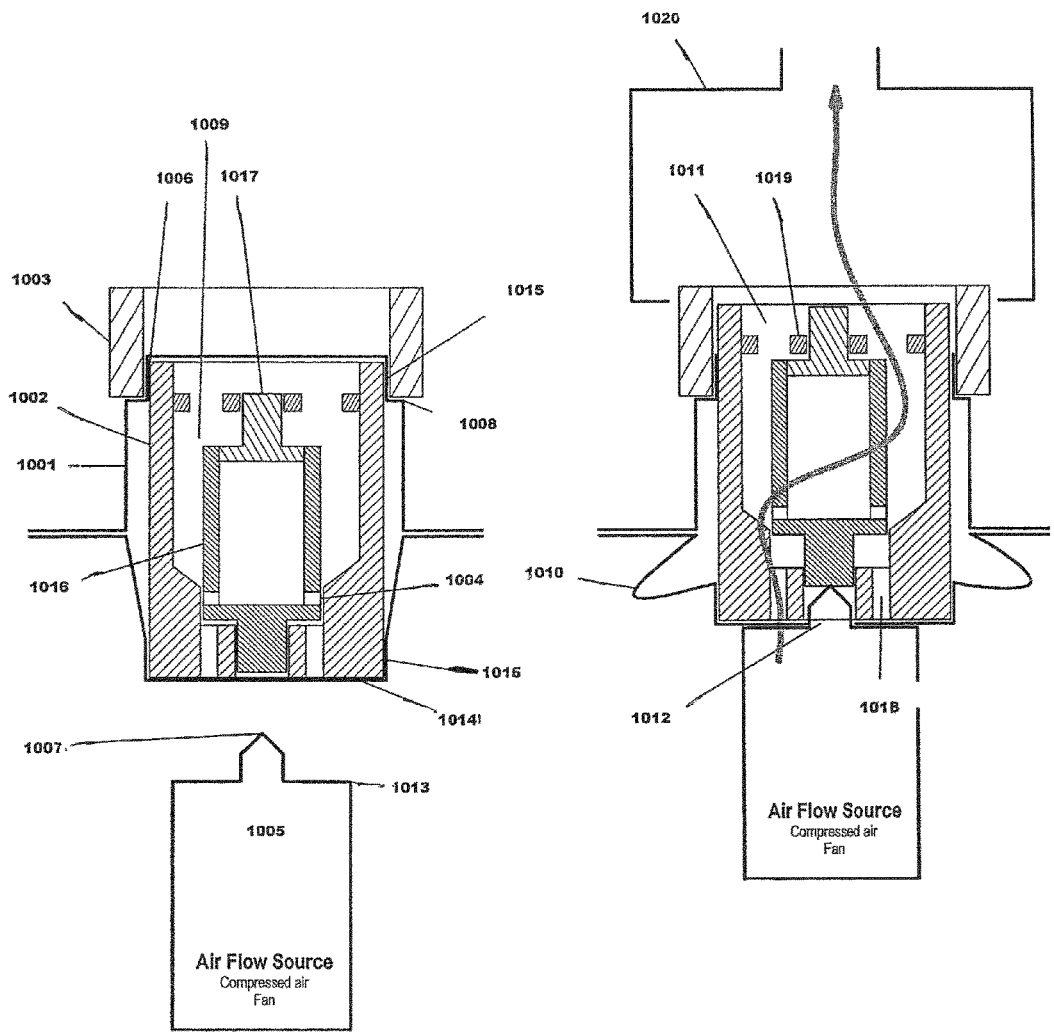
FIGS. 10A and 10B illustrate a drug delivery system similar to that of FIGS. 9A and 9B except it includes an active air flow source to assist in drug dispersion.

The spinning chamber drug package configuration can also be utilized in an active inhaler system. FIG. 10 shows this configuration and its use is identical to that of FIG. 9, with the difference being that rather than relying on the patient's respiration for the air flow to create the spinning action of second chamber 1016, an active compressed air or impellor system could be used. This may be particularly helpful in cases where the patient's air flow rate capabilities are diminished due to medical conditions. Correspondingly, with an active airflow source, it is envisioned that the entrained dose could be captured in a mixing chamber 1020 before being delivered to the user. The mixing chamber could be a rigid vessel or a flexible design that inflates during use and collapses for storage. The airflow through the package can be delivered through, or around, plunger 1005.

This design could also be applied in a combination dose configuration where multiple drugs are delivered to the patient at the same time.

Figure 11A:
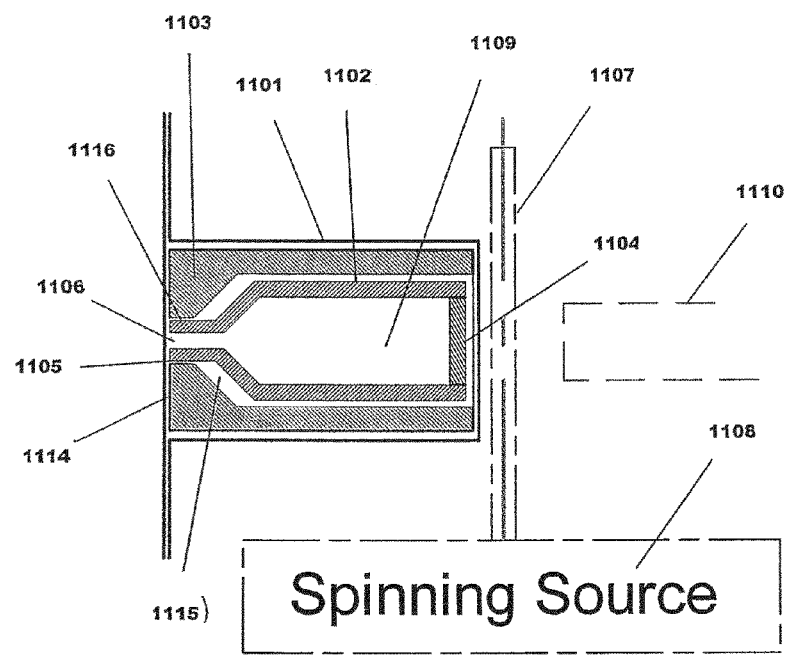
FIGS. 11A and 11B illustrate a drug delivery system that includes a spinning source to assist in drug dispersion.
Figure 11B:
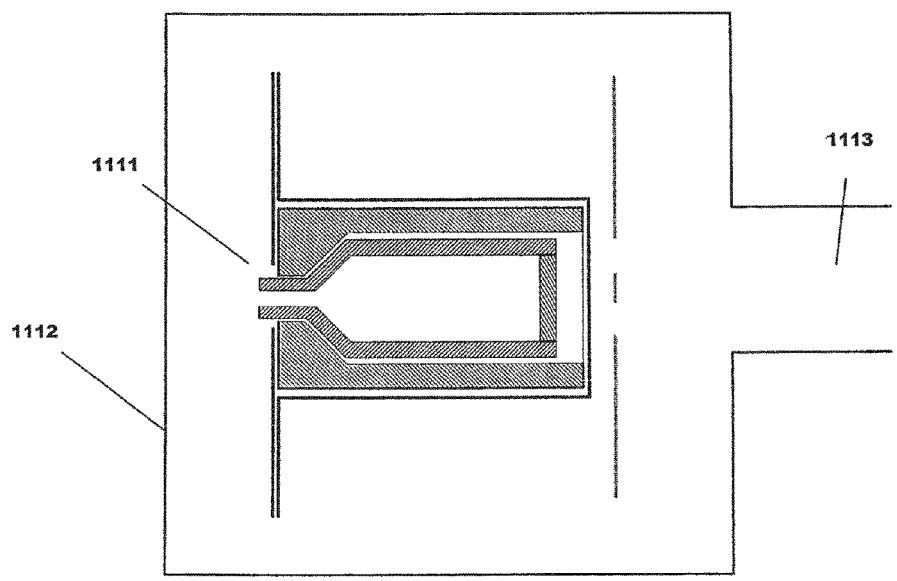
Figure 12B:
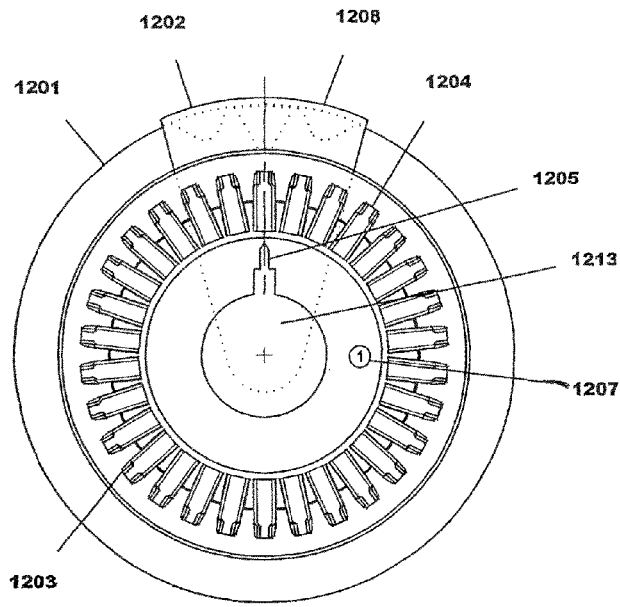
FIGS. 12A and 12B illustrate a multidose delivery system in an open and closed position.
Figure 12A:
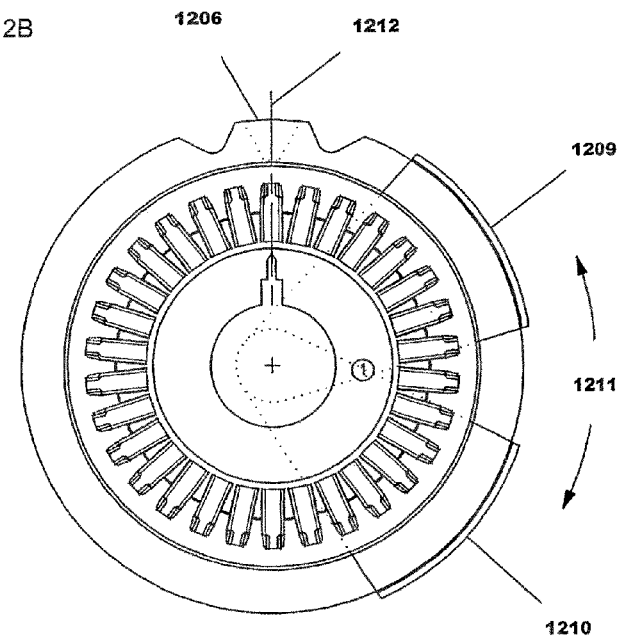

FIG. 11 illustrates a drug delivery device with a movable internal opening mechanism 1102 that contains the drug dose. Internal opening mechanism 1102 is located inside the drug sealing system 1103. Drug sealing system 1103 is located within moisture barrier 1101 and is attached at seal 1114, at least in part, to moisture barrier. Internal opening mechanism 1102 can move relative to moisture barrier 1101 and drug sealing system 1103. Moisture barrier 1101 is opened when cutting edge 1105 on internal opening mechanism 1102 is pressed against moisture barrier 1101. The drug dose exits through an opening 1106 by centrifugal force as the package is rotated (spinning action) about a main axis of rotation 1107. In alternate configurations, powder may also exit the internal opening mechanism by a venturi effect and/or by air flowing through internal opening mechanism 1102.

This configuration provides benefits including secure containment of the drug dose, ease of manufacturing and drug filling, and drug metering into the air stream.

Moisture barrier 1101 is comprised of two layers of a moisture impervious material, typically a plastic coated foil. The top and bottom layers of foil may be pre-formed to create the moisture barrier 1101 when attached together. Drug sealing system 1103 resides within moisture barrier 1101 and may create a first chamber 1115. The internal opening mechanism 1102 resides within first chamber 1115, and forms second chamber 1109. The drug dose resides inside second chamber 1109.

Second chamber 1109 has a plugged opening 1104 on one side for drug filling during manufacturing. The internal opening mechanism has a first cutting edge 1105 in close proximity to the foil of moisture barrier 1101. There is also a seal 1114 between drug sealing system 1103 and moisture barrier 1101 formed by means of a heat seal or interference fit. Internal opening mechanism 1102 creates a friction fit seal 1116 with drug sealing system 1103 to keep the drug from migrating out of second chamber 1109 prior to use. Drug sealing system 1103 may also extend around internal opening mechanism 1102 to guide its motion during opening of moisture barrier 1101.

To open the device package, internal opening mechanism 1102 is moved relative to moisture barrier 1101 so that first cutting edge 1105 pierces moisture barrier 1101. The motion of internal opening mechanism 1102 is caused by spinning the packaging device, creating centrifugal force which moves internal opening mechanism 1102 away from the axis of revolution 1107. In a passive system, the patient's inspiratory airflow would be used to spin the packaging device. In an active system, the spinning can be accomplished by means of an active spinning source 1108, such as a motor. An active configuration allows for stable control of rotational speed, and can provide higher opening speeds which allows thicker, formable foils to be used.

The speed at which piercing occurs can be controlled by a variety of factors, including the mass of internal opening mechanism 1102 and contained drug, the distance of the center of this mass from the axis of revolution 1107, the thickness of the moisture barrier 1101 foil layer, and the geometry of first cutting edge 1105. The ability to dictate the piercing speed has a number of potential benefits. In a passive system, where the rotation of the packaging device is caused by the patient's inspiratory air flow, the rotational speed at packaging device opening can be used to ensure that a minimum inspiratory flow rate is met prior to packaging device opening. In addition, in both passive and active systems, specific package opening speeds may allow for control of powder dispersion out of second chamber 1109 at predetermined rates.

Following piercing of moisture barrier 1101 by the internal opening mechanism 1102, the drug dose exits second chamber 1109 and is entrained in the air flow by means of centrifugal force. The rate of drug metering out of the packaging device can be controlled by means of the geometry of opening 1106 in internal opening mechanism 1102 as well as by the speed of rotation. It is envisioned that the drug dose may enter a mixing chamber 1112 before being delivered to the user. The drug exits mixing chamber 1112 through outlet mouthpiece 1113.

Piercing of moisture barrier 1101 by internal opening mechanism 1102 can also be achieved by means of an actuating mechanism 1110 rather than relying on centrifugal force caused by spinning of the device. This may be particularly useful in a passive system where it may be difficult to achieve high rotational speeds using the patient's inspiratory airflow alone.

This design could also be applied to a combination dose configuration where multiple drugs are delivered to the patient at the same time.

FIG. 12 illustrates a multi-dose drug delivery device that integrates the systems illustrated in FIGS. 1-11 and 13-14 and has the benefit of packaging multiple doses into a single dispensing system to simplify the user experience.

The dose packaging is manufactured in strips made up of multiple, factory pre-metered unit-doses 1204 that are positioned in a circular array and mounted between a two-piece clamshell cassette 1203. The dose packaging can be color coded to help identify drug type and dose strength.

The air path through each unit-dose is directed in an outward radial direction. A plunger 1205 is located at the center of cassette 1203 and has an outward motion during unit-dose packaging device opening. A mouthpiece 1206 is located on the outside of cassette 1203 and is aligned with the central axis of the first unit-dose 1212. A mouthpiece cover 1202 is attached to a mechanism 1213 designed to actuate plunger 1205, advance drug cassette 1203 and advance dose counter 1207.

Generally, to operate the multi-dose inhaler the user rotates mouthpiece cover 1202 from the closed position 1208 to a first position 1209, exposing mouthpiece 1206. The user then rotates mouthpiece cover 1202 to a second position 1210. This motion 1211 drives plunger 1205 in a radial direction, opening the unit-dose package 1204 that is aligned with plunger axis 1212. Plunger 1205 may be connected to mouthpiece cover 1202 by a mechanical linkage, or, alternatively, there may be a separate mechanism that causes the motion of the plunger that is not tied to the mouthpiece cover.

The user inhales to administer the drug dose, and then moves mouthpiece cover 1202 back to closed position 1208. The action of closing the mouthpiece cover advances unit-dose cassette 1203 to the second unit-dose position and advances dose counter 1207 by one number.

The multi-dose inhaler design also integrates a dose readiness indicator. The internal opening mechanism inside each dose package can be color coded for visibility. As each dose package is opened the internal opening mechanism is exposed and can be made visible to the user by means of a window in the cassette. Exposed color (green) can indicate that the dose is ready for inhalation.

Dose cassettes 1203 can be designed to be replaceable. In addition, the user can load cassettes with specific drug dose therapies by opening the cassette and replacing spent doses in a reusable configuration.

Figures 13A, 13B:
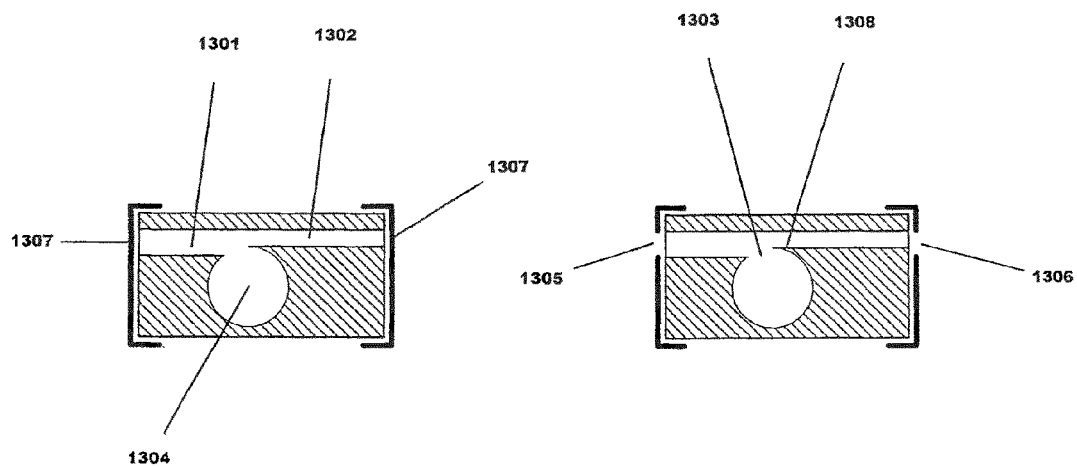
FIGS. 13A and 13B illustrate a simple variant of the drug delivery system using a shaped geometry to assist in dispersing the drug in the open and closed positions.

FIGS. 13A and 13B show a variant of the drug delivery system of the invention using a shaped dose metering system to assist in dispersing the medicine into the air path. FIG. 13A shows the device in the closed position while FIG. 13B shows it in the open position. The drug delivery system includes a first chamber, an opening device, and a dose metering system.

First chamber 1301 is comprised of two layers of material, typically a plastic. The top and bottom layers are pre-formed to create an air path 1302 when attached together. A dose metering system 1303 is formed into the walls of first chamber 1301 to assist in drug dispersion. The drug resides in a reservoir 1304 in proximity to dose metering system 1303 when the device is closed and the drug is dispersed into the air path after opening the device. Dose metering system 1303 is in the form of a geometry designed to divert, deflect or direct some portion of airflow from the first chamber into reservoir 1304. Reservoir 1304 is shaped to receive airflow diverted from the air path 1302 through first chamber 1301, causing the medicine to fluidize and move about reservoir 1304.

First chamber 1301 has air inlet 1305 and air outlet 1306, which are closed by barriers 1307 when the device is assembled. The airflow is managed by air channels formed by the first chamber and the geometry enclosing the air path.

An opening mechanism (not shown) punctures barriers 1307 to open the air pathway 1302. Air can be drawn through open air pathway 1302, and possibly through the opening mechanism, thereby entraining drug into the air stream. Dose metering system 1303 facilitates fluidization and dispersion of the drug.

Dose metering system 1303 includes a shaped opening 1308. Shaped opening 1308 has a geometry designed to control the movement of airflow in, out and around reservoir 1304 as air moves along air path 1302.

The drug delivery device shown in FIGS. 13A and 13B can readily be used in active configurations such as vibration and forced airflow source. Vibration from an "Active" source would facilitate drug dispersion. The active vibration source could be a piezo-electric actuator or a motor. The active configuration alternatively could use an active air flow source such as compressed air or a fan. In this case, the entrained dose would likely be captured in a mixing chamber before being delivered to the patient. The mixing chamber could be a rigid vessel or a flexible design that inflates during use and collapses for storage.

This design could also be applied in a combination dose configuration where multiple drugs are delivered to the patient at the same time. Typically, the drugs need to be stored separately from each other and then combined at the time of inhalation. This can be accomplished by dividing reservoir 1304 into multiple cavities, or by including multiple reservoirs 1304 within the device.

Figure 14A:
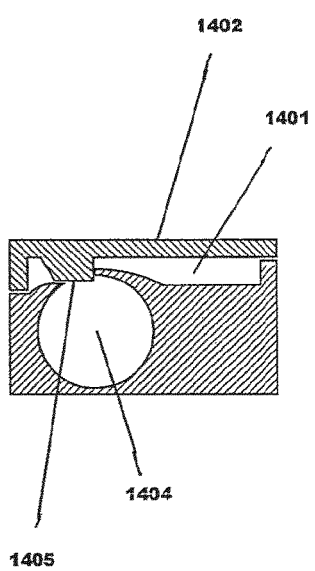
FIGS. 14A and 14B illustrate a variant of the drug delivery system of FIGS. 13A and 13B with an integral opening device in addition to the shaped geometry to assist in dispersing the drug in the open and closed positions.
Figure 14B:
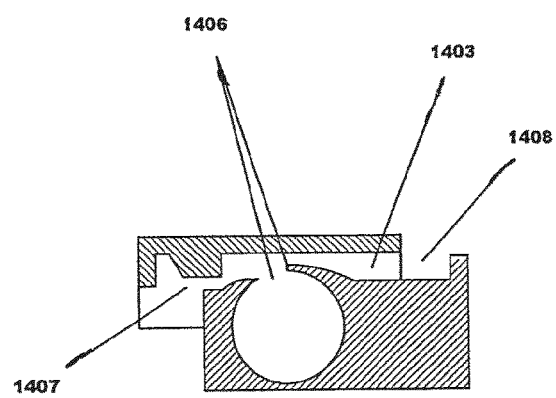

FIGS. 14A and 14B illustrate a drug delivery device that is similar to that of FIG. 13 except that the geometry of opening mechanism 1402 defines a portion of first chamber 1403 and air path 1401. Opening mechanism 1402 is movable from a closed position to an open position and is movable relative to reservoir 1404. This configuration provides benefits including secure containment of the drug. FIG. 14A shows the device in the closed position and FIG. 14B shows it in the open position.

First chamber 1403 is comprised of two parts and typically is made of plastic. In the illustrated embodiment, opening mechanism 1402 and first chamber 1403 are pre-formed to create a closed air path 1401. Air path 1401 has openings for air inlet 1407 and outlet 1408.

Reservoir 1404 contains the drug dose. Opening mechanism 1402 includes a drug sealing system 1405 that covers the opening to reservoir 1404 by interference fit when the device is stored in the closed position. Opening mechanism 1402 can be moved relative to reservoir 1404 to eliminate the interference at the opening to create an air path between first chamber 1403 and reservoir 1404. Integrated into first chamber 1403 is a drug metering system 1406 in the form of one or more shaped openings designed to fluidize powder in reservoir 1404 and facilitate drug entrainment into air path 1401.

Air path 1401 directs airflow past drug metering system 1406 and through the device. The air path can be shaped to create a restriction at the drug metering system, increasing velocity, and thereby increasing the effect of drug metering system 1406. Drug metering system 1406 is shaped to divert airflow into, and/or out of reservoir 1404, fluidizing the drug. Drug is entrained from the reservoir into the airflow by a combination of venturi effect, centrifugal force and turbulence created at the opening to the reservoir.

To open the device, opening mechanism 1402 is moved from the closed position to the open position. This action opens air path 1401 through first chamber 1403. This action also moves integral dose sealing system 1405 which opens up an air path between first chamber 1403 and reservoir 1404.

Air can be drawn through inlet opening 1407, through air path 1401, across drug metering system 1406 and out outlet opening 1408, entraining drug into the air stream. Dose metering system 1406, embodied by specific opening geometry in the reservoir, prevents the powder from leaving the package as one large clump and helps fluidize the dose.

This design could also be applied in a combination dose configuration where multiple drugs are delivered to the patient at the same time. Typically, the drugs need to be stored separately from each other and then combined at the time of inhalation. This can be accomplished by dividing reservoir 1404 into multiple cavities, or by including multiple reservoirs 1404 within the device.

The drug delivery device shown in FIGS. 14A and 14B can readily be used in active configurations such as vibration and forced airflow source. Vibration from an "Active" source would facilitate drug dispersion. The active vibration source could be a piezo-electric actuator or a motor. The active configuration alternatively could use an active air flow source such as compressed air or a fan. In this case, the entrained dose would likely be captured in a mixing chamber before being delivered to the patient. The mixing chamber could be a rigid vessel or a flexible design that inflates during use and collapses for storage.

The system of the present invention provides significant advantages not seen in the prior art. The system provides a sealed, protected environment for a substance and prevents exposure of the substance from degrading elements for an extended period of time. For example, the system can provide a moisture-impervious environment for moisture-sensitive substances, such as medicines in powdered form. The use of an integrated, internal puncturing mechanism (if applicable) facilitates release of the substance from the packaging device without relying on external components. The puncturing mechanism may be easily actuated, for example, by sliding the puncturing mechanism (i.e., the tube) within the internal chamber of the packaging device or a plunger may be used. The components of the packaging device are designed for manufacturability and the packaging device may be assembled and filled quickly and efficiently. The integrated puncturing mechanism provides a clear, unobstructed path for the substance stored in the packaging device to exit and reduces the number of dead spots or edges that trap the substance, a feature common in capsules that utilize external puncturing mechanisms. Moreover, the ability to create an air path through an internal chamber of a packaging device allows direct delivery of the substance, without requiring transfer of the substance to a separate delivery chamber. The integrated puncturing mechanism facilitates complete evacuation of all of the substance from the packaging device interior, resulting in more accurate dosing, increased safety and reduced waste.

The present invention has been described relative to illustrative embodiments. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall there between.

The invention claimed is:

1. A device for storing and delivering a medicine into an air path comprising:
   a first chamber that includes an air inlet and an air outlet and defines at least a first portion of an air path from the air inlet to the air outlet for delivery of medicament-entrained air to a user; and
   a second chamber that includes an outlet opening and is configured to retain medicament in the second chamber in an area that is sealed from the first portion of the air path of the first chamber;
   wherein the second chamber and the medicament are slidably movable relative to the first chamber from a closed position in which the outlet opening is closed to an open position in which the outlet opening is open to permit air flow into the second chamber and to open fluid communication between the first portion of the air path and the outlet opening of the second chamber, the second chamber being arranged in the open position to prevent clumps of medicament from exiting the second chamber to the air path of the first chamber and such that medicament-entrained air exiting the second chamber from the outlet opening enters the first portion of the air path at a restriction of the air path, and
   wherein the second chamber is constructed such that the outlet opening of the second chamber contacts the first chamber to close the outlet opening and seal the area from other portions of the first chamber to prevent release of said medicament into the air path when said second chamber is in the closed position.

2. The device of claim 1, further comprising a moisture impermeable barrier at least partially sealing the first portion of the air path in the first chamber from areas outside of the first chamber.

3. The device of claim 1, wherein said second chamber is internal to said first chamber.

4. The device of claim 1, wherein the second chamber includes a plurality of outlet openings that allow dispersion of medicine into the air path when said second chamber is in the open position.

5. The device of claim 1, wherein slidable movement of the second chamber relative to the first chamber is in a direction of air flow in the first portion of the air path at the restriction.

6. The device of claim 1, wherein the second chamber includes multiple second chambers each holding a respective medicament.

7. A device for storing and delivering a medicine into an air path comprising:
   a first chamber that includes an air inlet and an air outlet and defines at least a first portion and a second portion of an air path from the air inlet to the air outlet, the second portion for delivery of medicament-entrained air to a user; and
   a second chamber that includes an outlet opening and is configured to retain medicament in the second chamber in an area that is sealed from the second portion of the air path of the first chamber;
   wherein the second chamber and the medicament are slidably movable relative to the first chamber from a closed position in which the outlet opening is closed to an open position in which the outlet opening is open to permit air flow into the second chamber and to open fluid communication between the second portion of the air path and the outlet opening of the second chamber, the second chamber being arranged in the open position to prevent clumps of medicament from exiting the second chamber to the air path of the first chamber and such that air flow in the first portion of the air path is directed at medicament-entrained air exiting the second chamber from the outlet opening, and
   wherein the second chamber is constructed such that the outlet opening of the second chamber contacts the first chamber to close the outlet opening and seal the area from other portions of the first chamber to prevent release of said medicament into the air path when said second chamber is in the closed position.

8. The device of claim 7, further comprising a moisture impermeable barrier at least partially sealing the first portion of the air path in the first chamber from areas outside of the first chamber.

9. The device of claim 7, wherein said second chamber is internal to said first chamber.

10. The device of claim 7, wherein the second chamber includes a plurality of outlet openings that allow dispersion of medicine into the air path when said second chamber is in the open position.

11. The device of claim 7, wherein the second chamber is arranged in the open position such that medicament-entrained air exiting the second chamber from the outlet opening enters the first portion of the air path at a restriction of the air path, and wherein slidable movement of the second chamber relative to the first chamber is in a direction of air flow in the first portion of the air path at the restriction.

12. The device of claim 7, wherein the second chamber includes multiple second chambers each holding a respective medicament.

* * * * *